United States Patent [19]

Karasaki et al.

[11] 4,277,175
[45] Jul. 7, 1981

[54] METHOD AND APPARATUS FOR INSPECTING PRINTED WIRING BOARDS

[75] Inventors: Koichi Karasaki, Hadano; Yasuhiko Hara, Yokohama, both of Japan

[73] Assignee: Hitachi, Ltd., Tokyo, Japan

[21] Appl. No.: 74,473

[22] Filed: Sep. 11, 1979

[30] Foreign Application Priority Data

Apr. 25, 1979 [JP] Japan ................................. 54-50306

[51] Int. Cl.³ ............................................. G01B 11/00
[52] U.S. Cl. .................................... 356/378; 356/394
[58] Field of Search ........ 356/376, 378, 380, 384–387, 356/392–394, 398, 390, 237, 448; 250/560, 563

[56] References Cited

PUBLICATIONS

Krochmann et al., "Automatic Vector Distance Comparator VDK Projektina", Feinwertechnik & Messtechnik, vol. 84, 10, 11-76, pp. 330-334.

Primary Examiner—William H. Punter
Attorney, Agent, or Firm—Craig and Antonelli

[57] ABSTRACT

In order that a slight positional deviation of a plated through hole such as having no substantial effect on the function of wiring should not be optically detected as a defect in a printed wiring board, the plated through hole is recognized as a part of the wiring pattern by making light representative of the plated through hole nearly equal in intensity to reflected light from the wiring pattern. This is achieved by illuminating the printed wiring board with light from the back side or by placing a reflector on the back side of the printed wiring board.

9 Claims, 17 Drawing Figures

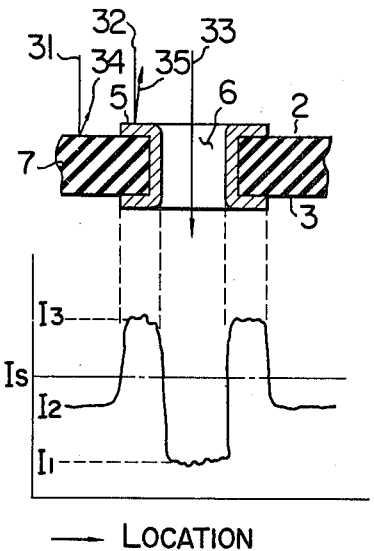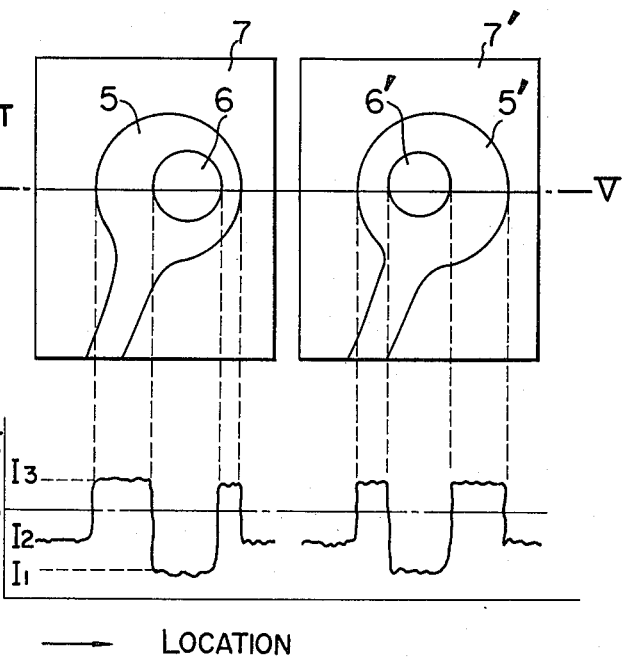

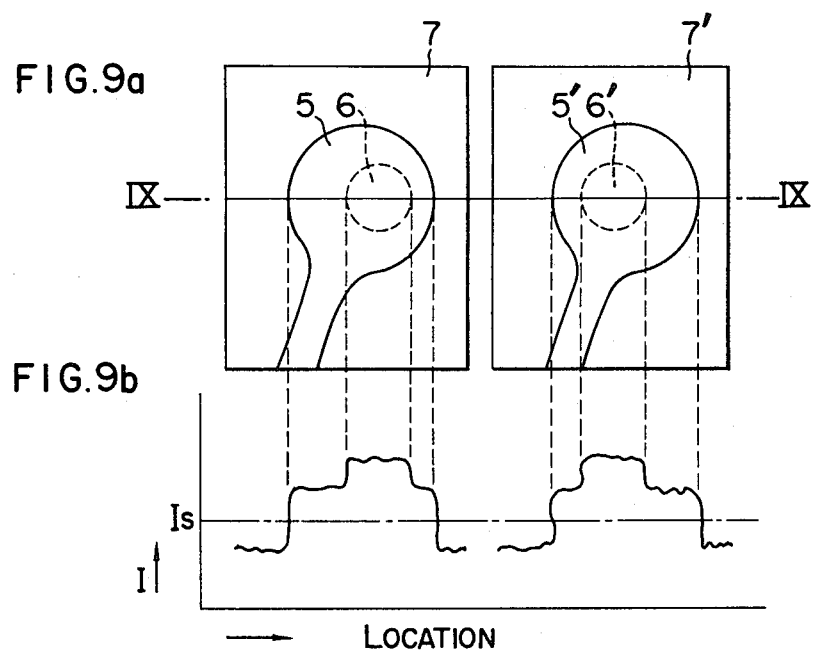
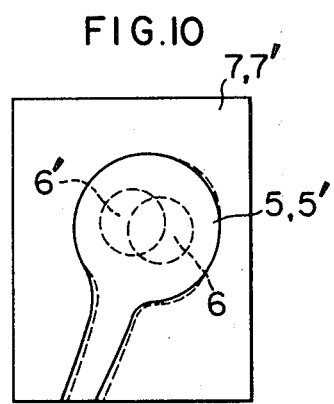

METHOD AND APPARATUS FOR INSPECTING PRINTED WIRING BOARDS

The present invention relates to a method and an apparatus for inspecting defects in a wiring pattern formed on a printed wiring board, and more particularly to a method and an apparatus for detecting defects which have been produced in the course of wiring pattern formation, by collating a wiring pattern on a printed wiring board with a wiring pattern on another printed wiring board.

In accordance with an aspect of the present invention there is provided a method for inspecting a printed circuit board including an insulating substrate having a wiring surface on which a wiring pattern is provided and including at least one plated through hole being in electrical connection with the wiring pattern and passing through the wiring board, the method comprising the steps of:

illuminating the wiring surface of the printed wiring board with light to obtain an optical image of the wiring surface at least by the use of reflected light from the wiring surface;

recognizing the optical images of the wiring pattern and plated through hole at the same level in the optical image of the wiring surface without distinguishing therebetween; and recognizing the optical image of the insulating substrate at a level different from that of the wiring pattern and the plated through hole to distinguish said optical image of the insulating substrate from those of the wiring pattern and the plated through hole.

In accordance with another aspect of the present invention there is provided an apparatus for inspecting printed wiring boards comprising:

first means for recognizing an optical image of a wiring surface of a printed wiring board, the optical image being formed at least by the use of reflected light from the wiring surface of the printed wiring board;

second means for recognizing an optical image of a wiring surface of another printed wiring board, the optical image being formed at least by the use of reflected light from the wiring surface of the another printed wiring board; and means for collating said optical images recognized respectively by the first and second recognizing means.

The present invention will now be described by way of example with reference to the accompanying drawings, in which:

FIGS. 4a, 4b, 5a, 5b and 6 are views for explaining a conventional method for inspecting printed wiring boards;

FIGS. 8a, 8b, 9a, 9b and 10 are views for explaining the operation of the embodiment shown in FIG. 7;

Figure 1:
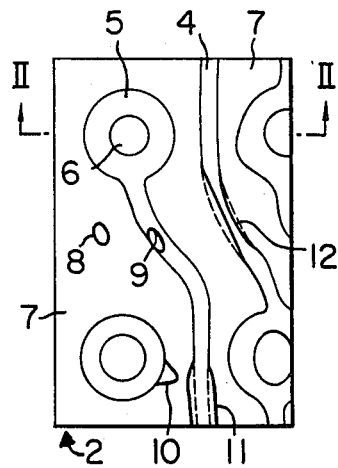
FIG. 1 is an enlarged plan view showing a part of a general printed wiring board.
Figure 2:
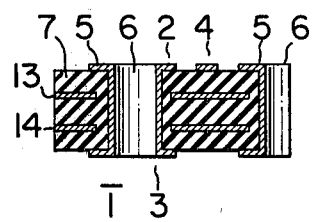
FIG. 2 is a sectional view taken along the line II—II in FIG. 1.
Figure 3:
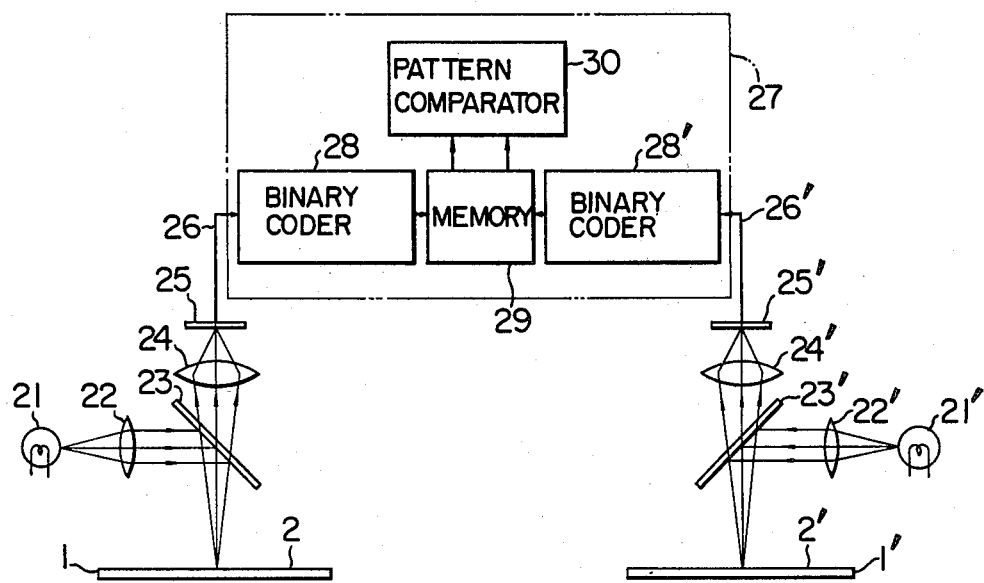
FIG. 3 is a schematic view showing a conventional apparatus for inspecting printed wiring boards.

Printed wiring boards generally have such a structure as shown in FIGS. 1 and 2 of the accompanying drawings. FIG. 1 is a plan view showing a wiring surface 2 of a printed wiring board 1, and FIG. 2 is a sectional view of the printed wiring board shown in FIG. 1, taken along the line II—II. In FIGS. 1 and 2, reference numerals 4 and 5 denote conductor pieces constituting a wiring pattern formed of a conductor foil such as a copper foil, 6 plated through holes for electrically connecting the wiring surface 2 with the back wiring surface 3, 7 an insulating substrate, and 13 and 14 conductor pieces constituting an internal layer pattern used respectively as ground and power layers and formed of a conductor foil such as a copper foil. The wiring pattern shown in FIG. 1 is formed by transferring a pattern which is indicated by solid lines (excepting heavy lines) and dotted lines in FIG. 1, on a copper foil in the form of an etching resist pattern by the use of a photographic plate (or a mask), and by etching the copper foil. When dust adheres to the photographic plate or a flaw is produced therein, there appear on the wiring pattern 2 a fine undesired pattern 8, a fine partial lack 9 of pattern, and a fine projection 10. Further, the thickening 11 or thinning 12 of pattern is produced according as the etching operation is performed insufficiently or excessively. Such defects as above give rise to various problems. That is, the fine partial lack 9 of pattern and the thinning 12 of pattern increase the electric resistance of the pattern, decrease the current capacity of the pattern, and give rise to disconnection when the printed wiring board is subjected to slight rubbing. The fine undesired pattern 8, the fine projection 10 and the thickening 11 of pattern give rise to a short circuit, or a solder bridge in soldering process. As a result, a correct (or desired) wiring cannot be formed on the printed wiring board. Specifically, in a recent high density mounting which employs, for example, a pattern width of 0.1 mm, it is required to detect the above-mentioned defects without overlooking them. However, since such detection cannot be made by visual inspection, the apparatus shown in FIG. 3 is employed in which an optical image is formed for each of the printed wiring boards 1 to be inspected and another printed wiring board 1' for comparison and collation to be compared and collated with each other. The conventional method employing the above-mentioned apparatus will be explained below. In FIG. 3 which shows a conventional apparatus for inspection of printed wiring boards, the same structures are arranged on the right and left sides with the exception of electrical-signal collating device 27, and the part on the right side corresponding to each of the parts on the left side is given the same reference numeral with prime. Explanation will not be made on the function and operation of each part on the right side, because the explanation thereof is given by replacing a reference numeral by the same reference numeral with prime in the following explanation made on the function and operation of each part on the left side. Above the wiring surface 2 of the printed wiring board 1 are disposed a half reflecting mirror 23 which reflects the horizontal light from a light source 21 to produce the light incident upon the wiring surface 2, and through which the reflected light from the wiring surface 2 travels upward, a refractor 24 which converges the light having passed through the mirror 23 to form an optical image, and a photodiode array 25 which is placed in an image forming plane and converts a pattern of light and darkness in the formed image into a multiplicity of electrical signals 26. Further, a collating device 27 is provided in which both the electrical signals 26 delivered from the left photodiode array 25 and the electrical signals 26′ delivered from a right-hand side photodiode array 25′ are recognized as wiring patterns, and are compared and collated with each other to point out the presence or absence of defects or positions where the defects exist. The positioning of each of the printed wiring boards 1 and 1′ is made by positioning means (not shown). Now, explanation will be made on a case where, for example, a printed wiring board shown in FIG. 4a is inspected. Referring to FIG. 3, the light emitted from the light source 21 is collimated by a refractor 22 to form parallel rays, directed downward by the half reflecting mirror 23, and then incident upon various portions on the wiring surface 2 of the printed wiring board 1 as light rays 31, 32 and 33 shown in FIG. 4a. The light ray 31 is reflected back as the reflected light ray 34 of a low intensity level due to a low reflectivity of the insulating substrate 7, the light ray 32 is reflected back as the reflected light ray 35 of a high intensity level due to a high reflectivity of the wiring pattern 5 made of a metal such as copper, and the light ray 33 does not give rise to reflected light because it goes past to the back wiring surface 3 through the plated through hole 6 or a perforation. The reflected light rays 34 and 35 which are directed upward, are incident upon the surface of the photodiode array 25 through the half reflecting mirror 23 and the refractor 24 to form an optical image. The photodiode array 25 includes a multiplicity of fine photodiodes (or light receiving elements) which are arranged on a straight line. For example, 256 photodiodes are arranged on a straight line as long as 5 mm. FIG. 4b is a waveform chart for showing electrical signals generated by the individual photodiodes when the light rays 34 and 35 form the optical image. In FIG. 4b, the abscissa designates the location of each photodiode of the photodiode array 25, and the ordinate the level of each of the electrical signals. Further, reference symbol $I_1$ denotes the level of electrical signals corresponding to the position of the plated through hole 6, which is low due to the absence of reflected light, $I_2$ the level of electrical signals into which the reflected light from the insulating substrate 7 is converted, which level is low but higher than $I_1$, and $I_3$ the level of electrical signals into which the reflected light from the wiring pattern 5 is converted, which level is high. In order to facilitate the comparison of these levels, it is necessary for these three levels to be converted into two kinds of levels (light and dark levels) or binary levels. For this reason, there is provided a binary coder 28 which is formed of, for example, a voltage comparator, and which translates an electrical signal having a signal level higher than a level $I_s$ (shown in FIG. 4b) to the light level and an electrical signal of a signal level lower than the level $I_s$ to the dark level. Thus, the electrical signals based upon the wiring pattern 5 are translated to the light level (or "1" level of binary code), and those based upon the insulating substrate 7 and plated through hole 6 are translated to the dark level (or "0" level of binary code). That is, the electrical signals delivered from the photodiode array 25 are converted into binary signals. The binary signals thus obtained form linear information (that is, such linear information as viewing the pattern of FIG. 5a across the line V—V), since the light receiving surface of the photodiode array 25 has a form of a line. Accordingly, by storing these binary signals in a memory 29 while displacing the printed wiring board 1 in parallel in the plane containing the wiring surface 2, the plane information can be obtained. Then, the plane information on the wiring surface 2 and that on the wiring surface 2′, both of which have been stored in the memory 29, are collated with each other at a pattern comparator 30 to indicate those parts which correspond to but are incongruous with each other, as a defect.

Figure 6:
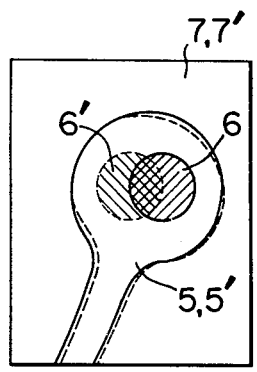

According to the above-mentioned method for inspection, any defect is precisely pointed out based upon the difference between wiring patterns. However, this method detects even such a little deviation in position between the plated through hole and the wiring pattern as having no substantial effect on the property of wiring (such as the electrical resistance, the current bearing capacity, or the presence or absence of a solder bridge in the soldering process) and treats such a positional deviation as a defect. As a result, the yield of printed wiring boards becomes low, and moreover the lowering of yield is specifically remarkable in the case of high density mounting. Now, explanation will be made on a case where a little positional deviation is generated between the plated through hole and the wiring pattern, by reference to FIGS. 5a, 5b and 6. FIG. 5a shows patterns which are formed by binary data stored in the memory 29, and the left and right patterns show cases where the plated through hole is a little deviated respectively to the right and left. FIG. 5b shows the level of electrical signals at a time when the photodiode arrays 25 and 25′ are placed on the line V—V of FIG. 5a. The abscissa and ordinate of FIG. 5b have the same meaning as in FIG. 4b. FIG. 6 shows a state that two binary patterns shown in FIG. 5a are superposed to be compared with each other. As can be seen in FIG. 6, the insulating substrates 7 and 7′ are at the same dark level and congruous with each other, and the wiring patterns 5 and 5′ are also congruous with each other. However, those portions of the plated through holes 6 and 6′ which are indicated by the oblique lines except the overlapped portion are incongruous with each other (that is, each portion is translated to the dark level in one of the binary patterns, and translated to the light level in the other binary pattern), and are indicated as a defect.

An object of the present invention is to provide a method and an apparatus which can almost eliminate the above-mentioned drawbacks of conventional techniques and can detect any positional deviation between two wiring patterns without detecting, as a defect, a relative deviation in position between a plated through hole and a wiring pattern.

A main feature of the present invention which achieves the above-mentioned and other objects, resides in that the detection of a positional deviation between a plated through hole and a wiring pattern is prevented by recognizing the through hole and the wiring pattern at the same light level. In more detail, the detection of the positional deviation of plated through hole is prevented in the following manner. That is, in one embodiment of the present invention, on the back side of a printed wiring board is provided a light reflector which reflects back the light having passed through a plated through hole to the surface side of the printed wiring board. Further, in another embodiment of the present invention, both of the surface and the back side of a printed wiring board are illuminated with light.

Figure 7:
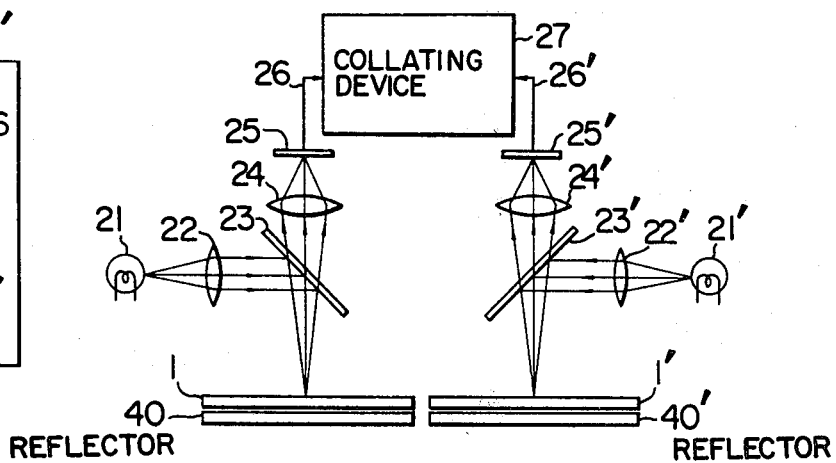
FIG. 7 is a schematic view showing an embodiment of an apparatus for inspecting printed wiring boards according to the present invention.

Now, preferred embodiments of the present invention will be explained below in detail by reference to the drawings. FIG. 7 shows an embodiment of an apparatus according to the present invention, and FIGS. 8 to 10 are views for explaining the operation of the above embodiment. In FIG. 7, reference numerals 40 and 40' designate reflectors. Each reflector reflects back the light which is incident from above upon the surface of a printed wiring board 1 or 1' and passes through a plated through hole, in such a manner that the reflected light travels upwards and passes again through the plated through hole. For the reflectors 40 and 40' may be used a mirror which effects total reflection, a plate coated with a white paint having a relatively high reflectivity, a white paper, or the like. Sinc other parts 21 to 27 and 21' to 26' in FIG. 7 are the same as those in FIG. 3, the explanation thereof is omitted.

Figure 8A:
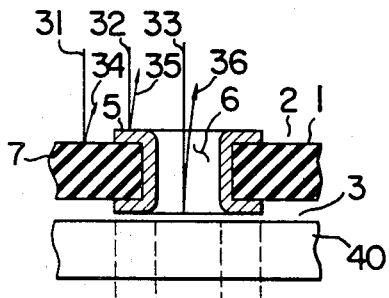
Figure 8B:
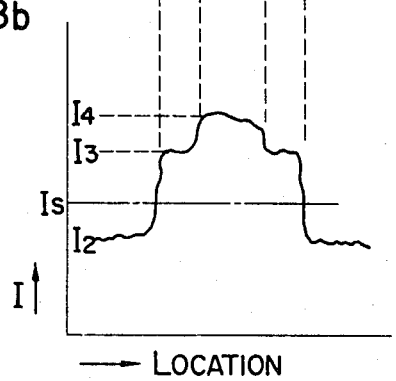

In a case where such a printed wiring board 1 as shown in FIG. 8a is inspected, the light emitted from the light source 21 (shown in FIG. 7) is collimated by the refractor 22 to form parallel light rays, directed downward by the half reflecting mirror 23, and then incident upon various portions of the wiring surface as light rays 31, 32 and 33 shown in FIG. 8a. The light ray 31 is reflected back from the insulating substrate 7, and the reflected light ray 34 is at a low intensity level due to a low reflectivity of the insulating substrate. The light ray 32 is reflected back from the wiring pattern 5 made of such a metal as copper, and the reflected light ray 35 is at a high intensity level due to a high reflectivity of the wiring pattern. The light ray 33 passes through the plated through hole 6 (or a perforation) and then is reflected back from the reflector 40, and the reflected light ray 36 has a high intensity due to a high reflectivity of the reflector 40. These reflected light rays 34, 35 and 36, as shown in FIG. 7, are incident upon the under surface of the photodiode array 25 through the half reflecting mirror 23 and the refractor 24 to form an optical image. The electrical signals delivered from the photodiode array 25, on which the optical image is formed, have such signal levels as shown in FIG. 8b. That is, the reflected light ray 34 from the insulating substrate 7 is converted into a signal of a low level $I_2$, the light ray 35 reflected back from the wiring pattern 5 is converted into a signal of a high level $I_3$, and the reflected light ray 36 having passed through the plated through hole 6 is converted into a signal of a high level $I_4$. The abscissa and ordinate in FIG. 8b have the same meaning as those in FIG. 4b. The above-mentioned three levels are converted by the collating device 27 into two levels, that is, the levels $I_3$ and $I_4$ higher than a level $I_s$ are at the light level, and the level $I_2$ lower than the level $I_s$ is at the dark level. Further, the plane information is obtained in the same manner as explained previously, and two binary patterns are compared with each other. FIG. 9b shows the level of electrical signals which are delivered from the photodiode arrays 25 and 25' relatively moving along the line IX—IX on the printed wiring boards 1 and 1' having the illustrated patterns. The electrical signals of a level higher than the level $I_s$ are at the light level, and the electrical signals of a level lower than the level $I_s$ are at the dark level. That is, the electrical signals delivered from the photodiode arrays are converted into binary signals. These binary signals are used to form the plane information, namely, the binary patterns shown in FIG. 9a. As shown in FIGS. 9a and 9b, the output signals of the photodiode arrays 25 and 25' based upon the plated through holes 6 and 6' are different in level from those based upon the wiring patterns 5 and 5'. However, these two kinds of output signals having levels higher than the level $I_s$, are both at the light level, and therefore cannot be distinguished from each other. Incidentally, the abscissa and ordinate in FIG. 9b have the same meaning as those in FIG. 4b. When two binary patterns shown in FIG. 9a are superposed, the plated through holes 6 and 6' (indicated by dotted lines) cannot be distinguished from the wiring patterns 5 and 5', as shown in FIG. 10. Accordingly, no positional deviation between the plated through holes 6 and 6' and the wiring patterns 5 and 5' can be detected. However, since other parts of the printed wiring boards 1 and 1' than the plated through holes 6 and 6' are distinguishable from each other, it is possible to detect such defects as the positional deviation of wiring pattern, the formation of a fine undesired pattern, the partial lack of pattern, and the thickening and thinning of pattern. The above embodiment makes use of the light which passes through a plated through hole and is then reflected back from a reflector. Accordingly both a signal layer printed wiring board and a double layer printed wiring board each employing a transparent substrate can be inspected according to this embodiment.

Figure 11:
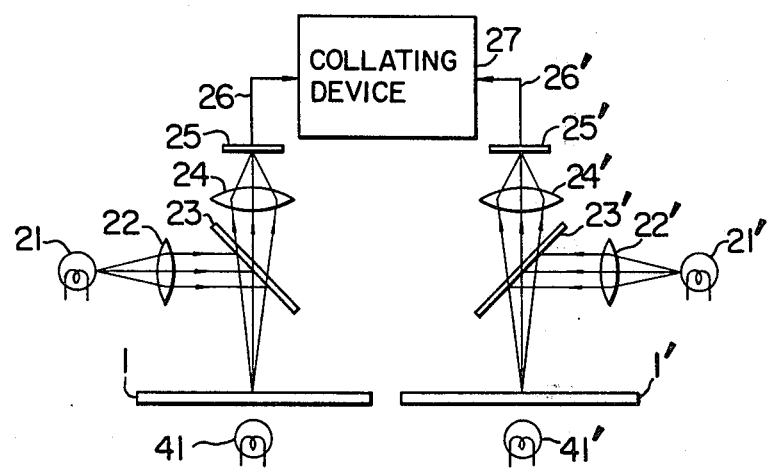
FIG. 11 is a schematic view showing another embodiment of an apparatus for inspecting printed wiring boards according to the present invention.
Figure 12A:
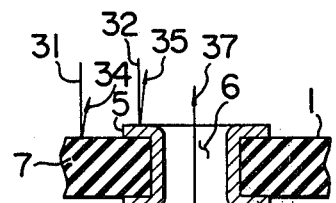
FIGS. 12a and 12b are views for explaining the operation of the embodiment shown in FIG. 11.
Figure 12B:
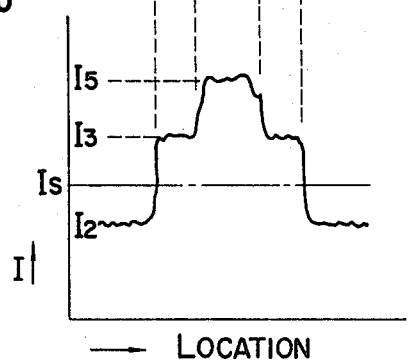

FIG. 11 shows another embodiment of an apparatus for inspection of printed wiring boards according to the present invention, and FIGS. 12a and 12b are views for explaining the operation of the above embodiment. In FIG. 11, reference numerals 41 and 41' designate light sources each for generating a light ray 37 which passes through the plated through hole 6 in place of the reflected light ray 36 shown in FIG. 8a. The light ray 37 having passed through the plated through hole is required to have such an intensity as producing an electrical signal of the light level, and it is desirable to make the light ray 37 parallel to the axis of the plated through hole. Since other parts 21 to 27 and 21' to 26' in FIG. 11 are identical with those in FIG. 3, the explanation thereof is omitted. In a case where such a printed wiring board 1 as shown in FIG. 12a is subjected to inspection, the light ray 34 reflected back from the insulating substrate 7, the light ray 35 reflected back from the wiring pattern 5, and the light ray 37 emitted from the light source 41 are converted by the photodiode array 25 or 25' into an electrical signal of level $I_2$, an electrical signal of level $I_3$, and an electrical signal of level $I_5$, respectively. These electrical signals are converted into binary signals by, for example, a voltage comparator employing a level $I_s$ as a reference level, and then used to form the previously mentioned plane information which includes two binary patterns to be compared with each other. The binary patterns are the same as those shown in FIG. 9a, and are superposed as shown in FIG. 10. As has been explained in connection with FIGS. 9a, 9b and 10, the plated through holes 6 and 6' (indicated by dotted lines in FIG. 10) cannot be distinguished from the wiring patterns 5 and 5'. Accordingly, any positional deviation between the plated through hole and the wiring pattern cannot be detected in the collating process. Since other parts of the printed wiring boards 1 and 1' than the plated through holes are distinguishable from each other, it is possible to detect, through comparison and collation, such defects as the positional deviation of pattern, the formation of a fine undesired pattern, the partial lack of pattern, and the thickening and thinning of pattern. The above embodiment is simple in construction, since the positional deviation of the plated through hole is allowed by merely employing light sources placed beneath printed wiring boards.

As has been explained hereinbefore, according to the present invention, two patterns are collated with each other under such a condition that a plated through hole has been recognized as a part of a wiring pattern. Accordingly, the present invention allows the positional deviation of the plated through hole, but can detect various defects such as the positional deviation of pattern, the formation of a fine undesired pattern, the partial lack of pattern, and the thickening and thinning of pattern, and therefore can remarkably enhance the yield of printed wiring boards.

What we claim is:

1. A method of inspecting a printed wiring board including and insulating substrate having a wiring surface on which a wiring pattern is provided and including at least one plated through hole being in electrical connection with said wiring pattern and passing through said wiring board, the method comprising the steps of:

illuminating said wiring surface of said printed wiring board with light to obtain an optical image of said wiring surface at least by the use of reflected light from said wiring surface;

recognizing the light intensity of the optical images of said wiring pattern and that of the plated through hole as being at an identical first level of two digitized levels in said optical image of said wiring surface without distinguishing therebetween; and recognizing the light intensity of the optical image of said insulating substrate as being at a second level of said two digitized levels different from that of said light intensity of said wiring pattern and said plated through hole to distinguish said optical image of said insulating substrate from said images of said wiring pattern and said plated through hole.

2. A method according to claim 1, wherein the back side of said printed wiring board is illuminated with light capable of bringing said optical image of said plated through hole at the same light level as said optical image of said wiring pattern.

3. A method according to claim 1, wherein light having passed through said plated through hole to the back side of said printed wiring board is reflected back from a reflector capable of producing reflected light which is directed to said plated through hole and can bring said optical image of said plated hole at the same light level as said optical image of said wiring pattern.

4. An apparatus for inspecting printed wiring boards, comprising:

first means for recognizing an optical image of a wiring surface of a printed wiring board, said optical image being formed at least by the use of reflected light from said wiring surface of said printed wiring board;

second means for recognizing an optical image of a wiring surface of another printed wiring board, said optical image being formed at least by the use of reflected light from said wiring surface of said another printed wiring board; and means for collating said optical images recognized respectively by said first and second recognizing means, wherein each of said first and second optical-image recognizing means includes a binary coder for converting both an optical image of a wiring pattern and an optical image of a plated through hole into signals of an identical first level of two digitized light levels and for converting an optical image of an insulating substrate into a signal of a second level of said two digitized light levels different from said first level.

5. An apparatus according to claim 4 including a first light source for generating light incident upon each of said wiring surfaces to form an optical image of said wiring surface, and a second light source for generating light travelling from the back side of each of said printed wiring boards to each of said first and second optical-image recognizing means through said plated through hole.

6. An apparatus according to claim 4, including a light source for generating light incident upon each of said wiring surfaces to form an optical image of said wiring surface, and a reflector placed in close vicinity to the back side of each of said printed wiring boards for reflecting back light arriving at said back side through said plated through hole, to produce reflected light directed to said plated through hole.

7. An apparatus according to claim 6, wherein said reflector is a mirror.

8. An apparatus according to claim 6, wherein said reflector is a plate coated with a white paint having a high reflectivity.

9. An apparatus according to claim 6, wherein said reflector is a plate having a white paper provided on the surface thereof.

* * * * *